United States Patent [19]

Carr et al.

[11] Patent Number: 5,466,825
[45] Date of Patent: Nov. 14, 1995

[54] ARYL IMIDO SUBSTITUTED PEROXYCARBOXYLIC ACIDS

[75] Inventors: Graham Carr, Woolton; Paul R. Harrison, Penketh; Alun P. James, Blundellsands, all of England

[73] Assignee: Solvay Interox Limited, Warrington, England

[21] Appl. No.: 78,172

[22] PCT Filed: Dec. 19, 1991

[86] PCT No.: PCT/GB91/02280

§ 371 Date: Jun. 18, 1993

§ 102(e) Date: Jun. 18, 1993

[87] PCT Pub. No.: WO92/11238

PCT Pub. Date: Jul. 9, 1992

[30] Foreign Application Priority Data

Dec. 22, 1990 [GB] United Kingdom ............... 9027975

[51] Int. Cl.[6] .................................. C07D 209/48
[52] U.S. Cl. .................. 548/479; 252/96; 252/100; 8/111
[58] Field of Search ................. 548/479; 252/100, 252/96; 8/111

[56] References Cited

U.S. PATENT DOCUMENTS

| 4,119,660 | 10/1978 | Hutchins | 562/6 |
| 4,172,086 | 10/1979 | Berkowitz | 562/6 |
| 4,233,235 | 11/1980 | Camden et al. | 562/6 |
| 4,337,213 | 6/1982 | Marynowski et al. | 568/566 X |
| 5,208,340 | 5/1993 | Cavallotti et al. | 546/98 |

FOREIGN PATENT DOCUMENTS

| 0325288 | 7/1989 | Germany. |
| 0349940 | 1/1990 | Germany. |
| 9007501 | 7/1990 | WIPO. |
| 9014336 | 11/1990 | WIPO. |

Primary Examiner—Jacqueline Haley
Attorney, Agent, or Firm—Larson and Taylor

[57] ABSTRACT

Peroxycarboxylic acids of formula (I) are disclosed wherein the substituents are defined by the disclosure. The peroxycarboxylic acids are useful for washing, bleaching and disinfecting, and methods for using them in such processes are also disclosed. Further, a process for preparing the peroxycarboxylic acids is disclosed.

$$X \underset{C}{\overset{C}{\underset{\diagdown}{\bigcirc}}} \underset{C-C}{\overset{C-C}{\diagup}} \underset{\diagdown}{\overset{\diagup O}{\underset{\diagdown O}{\diagup}}} N-(CHY)_x - \underset{\underset{Y}{|}}{\overset{Ph}{\underset{|}{C}}} - (CHY)_y - C \underset{O-O-H}{\overset{\diagup O}{\diagdown}} \quad (I)$$

16 Claims, No Drawings

ARYL IMIDO SUBSTITUTED PEROXYCARBOXYLIC ACIDS

This application is a National Stage application of PCT/GB91/02280 filed Dec. 19, 1991, now WO 92/11238, published Jul. 9, 1992.

The present invention relates to peroxycarboxylic acids and more particularly to peroxycarboxylic acids which contain within their structure an imido linkage, to the preparation of such percarboxylic acids and to their use in bleaching compositions and in washing compositions.

Organic peroxycarboxylic acids, sometimes alternatively called percarboxylic acids or organic peracids, as a class, are potentially very useful oxidising agents as a result of their high electropotential which enables them to bleach very effectively a wide range of stains that mark domestic laundry or non-absorbent surfaces in the home and very useful disinfectants or sanitizers on account of their biocidal activity against a broad spectrum of pathogenic micro-organisms. Self-evidently, some percarboxylic acids are more effective than others in such activities, but the relative efficacy of the percompounds is only one key factor in determining the potential usefullness of such percompounds because they vary also in a second key area, which is the physical characteristics of the percompounds and specifically their sensitivity to impact, pressure or thermal shock and their propensity to decompose during storage, either by themselves or in contact with other components of washing or bleaching compositions. Variation in respect of both factors occurs as a direct result of what else is present in the percarboxylic acid molecule and the structural relationship of for example the miscellaneous substituents to the percarboxylic acid group and to each other.

It is very easy for the skilled person in this field to set out his criteria for a very acceptable peroxyacid, namely effective washing and bleaching performance whilst offering sufficient resistance to impact, pressure and thermal shocks and a long shelf-storage life, i.e., successful, safe and stable, but it is not at all easy to predict from the formula alone the extent to which many sub-classes of peroxyacid attain those criteria, despite the impression fostered by the presence of general formulae for peracids in many patent specifications, e.g. U.S. Pat. No. 4,259,201 of HO-O-(CO)-R-Y which appear to equate aliphatic and aromatic peroxyacids and a wide range of substituents. None the less, as the present investigations into the preparation of a wide range of peroxyacids and their properties progressed, the present investigators became aware of certain correlations within any given sub-class of peroxyacids.

One of the sub-classes of peroxyacids tested in the course of the present investigations comprised those containing within their structure an imide link. In the last year or so, applications have been published in the names of Interox Chemicals Limited (PCT/GB 89/01524), Hoechst (EP-A-0 349 940) and Ausimont spa (EP-A-0 325 288 and EP-A-0 325 289) relating to phthalimidoalkylperoxycarboxylic acids as such and/or for use as a bleach. A few of the compounds described in those applications meet to a reasonable extent the desideratum of simultaneously exhibiting the chemico-physical properties of good storage stability and safe handling with good bleaching and disinfection performance. As a result of conducting a range of comparative tests on the imidoperoxyacids, the instant inventors concluded that the imidoperoxyacid exhibiting the best combination of properties comprised phthalimido-6-peroxyhexanoic acid, alternatively referred to by some as phthalimidoperoxycaproic acid or its abbreviation PIPCA or PAP.

None the less, the instant inventors continued to seek products that are superior to PIPCA and have now discovered a range of compounds that is related to PIPCA, but shows enhanced washing performance.

According to the present invention there is provided an organic peroxyacid which satisfies general formula (1):

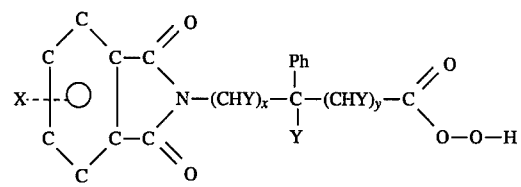

in which X represents hydrogen or a compatible non-released substituent, Y represents a group of formula $(CH_2)_zH$, x, y and z are either 0, 1 or 2, and x+y+z= 1 or 2, and Ph represents a phenyl substituent, optionally substituted by a compatible non-released substituent.

The peroxyacids according the formula of the instant invention advantageously manifest improved washing/bleaching capabilities and in particular in respect of the types of stains against which previous generations of peroxyacids have been relatively unsuccessful. Those stains, like grass or polish tend to be relatively hydrophobic. It will accordingly be recognised that instant invention provides peroxyacids which combine the practical benefits of acceptable stability and safe handling with improved bleach performance against hydrophobic stains.

Each occurrance of Y can be the same or different. In one set of favoured compounds, y=1, in another set z=0 and in a third set, x and z both=0 and y=1.

In the general formula, X can very conveniently represent hydrogen. Alternatively, X can represent a non-released compatible substituent such as a low molecular weight alkyl substituent, e.g., methyl to propyl, or a halo substituent, such as chloro or bromo, which is preferably at the 4 or 5 position around the nucleus.

In a number of desirable compounds according to the present invention, the phenyl substituent Ph is unsubstituted. However, in some other desirable compounds when X=H, Ph can itself be substituted by one of the group of non-released compatible substituents described hereinabove for X.

In a particularly desirable peroxyacid, x and z=0, y=1, X=H and Ph is unsubstituted.

The invention peroxycarboxylic acids can be made by reaction between the corresponding carboxylic acid and hydrogen peroxide in a strong mineral acid or organic acid reaction medium at a reaction temperature of below about 50° C., such as from −5° C. to 50° C., preferably from 5° to 30° C. maintained until peroxyacid product precipitates out of solution, and thereafter separating the product from the reaction medium.

Similar reaction procedures are known for making poorly soluble aliphatic peroxyacids, and these can be applied to the manufacture of the invention peroxyacids. In effect, the teaching in such prior publications as Siegel, et al in JOC, vol 27 pp 1336–42 in 1961 entitled Peroxides IX. New Method for the Direct Preparation of Aromatic and Aliphatic Peroxyacids" can be employed, but modified as to the carboxylic acid starting materials. Likewise, various processes described for the production of aliphatic peroxyacids in each of U.S. Pat. No. 2,813,896 (Krimm) U.S. Pat. No. 4,119, 660 (Hutchins), U.S. Pat. No. 4,172,086 (Berkowitz), U.S. Pat. No. 4,233,235 ( Camden), and U.S. Pat. No.

4,337,213 (Marynowski). Thus, the reaction medium for the peroxidation reaction when organic, is especially suitably an organic sulphonic acid, such as specifically methane sulphonic acid, which is probably the most readily available lower alkane sulphonic acid. When the reaction medium is a mineral acid, it is most preferably sulphuric acid or can desirably be at least partly phosphoric acid. Mixtures of the strong acids can be employed if desired.

It will also be recognised that where the reaction medium comprises a mineral acid, such as sulphuric acid, all or part of it can be premixed with the hydrogen peroxide to form an equilibrium mixture containing for example permonosulphuric acid that can itself perform the peroxidation reaction. Such premixing is beneficial because it separates the exothermic dilution/reaction between hydrogen peroxide and sulphuric acid from the peroxidation reaction, thereby enabling both to be controlled more readily and safely.

In a further aspect of the present invention there is provided a method for making peroxyacids in which the corresponding carboxylic acid is reacted with aqueous hydrogen peroxide in a sulphuric acid reaction medium characterised in that in step (1) an aqueous reaction medium having a predetermined acidity is formed by mixing aqueous hydrogen peroxide with concentrated sulphuric acid, said acidity being selected in the range of from 60% to 90% such that it is below the acidity at which the mixture containing peroxyacid product is hazardous, in step (2) the carboxylic acid is dissolved in concentrated sulphuric acid having an acidity higher than the acidity of the reaction mixture and in step (3) the product of step (2) is introduced gradually with stirring at a temperature of below about 40° C. into the reaction mixture formed in step (1) and the acidity of the reaction medium maintained substantially constant by the introduction of an aqueous diluent.

It has been found that such a method represents a particularly effective way of utilising a sulphuric acid reaction medium for the preparation of peroxyacids according to formula (1) herein.

By carrying out such a preparative method, it is possible to combine the advantage of employing a reaction medium which at all times has an acidity that is non-hazardous with the use of concentrated sulphuric acid as the solvent for the carboxylic acid.

The acidity of the reaction medium is an extremely important factor in governing the rate at which the peroxidation reaction occurs. In consequence, it is preferable to select an acidity which is as high as possible, without reaching the acidity at which the reaction mixture containing peroxyacid product would become hazardous, and indeed allowing also a suitable safety margin. The maximum acidity for the medium will vary depending upon the peroxycarboxylic acid. In the case of peroxyacids according to formula (1) herein, the maximum acidity is in the region of about 75% by weight calculated using the formula $S/(S+W)$ where S and W represent respectively sulphuric acid and water, including any sulphuric acid that has been converted to permonosulphuric acid.

For making peroxyacids according to formula (1) herein, the acidity is preferably selected in the region of 70 to about 75% and most preferably is around 75%.

Step (1) can be carried out by controlled mixing of concentrated hydrogen peroxide with concentrated sulphuric acid, the temperature of the mixture being maintained at or below or subsequently brought to the reaction temperature of step (3). Methods for making such mixtures are known in themselves.

Step (2) preferably employs aqueous sulphuric acid of at least 90% strength and conveniently from 94 to 98% strength. By employing such strength acid, its volume can be minimised whilst still dissolving all the carboxylic acid. Were a more dilute sulphuric acid solution to be employed as solvent, the overall volume of the solution would be increased, thereby affecting product recovery. It is often desirable to produce a solution in step 2 that contains at least 80% of the saturated concentration of carboxylic acid.

It will be recognised that in step (3), the acidity of the reaction medium would increase if a counterbalancing amount of an aqueous diluent were not employed. The amount of such diluent naturally can be calculated easily knowing the acidity of the materials produced in steps (1) and (2). The most convenient aqueous diluent comprises water, but it will be recognised that it can contain, if desired, hydrogen peroxide or even be a dilute solution of sulphuric acid.

It is desirable to employ overall a substantial excess of hydrogen peroxide, preferably in excess of 3 moles per mole of carboxylic acid and often from 4 to 7.5 moles per mole of carboxylic acid. The ratio does not distinguish between hydrogen peroxide itself and that which has been converted to permonosulphuric acid. This can usually be obtained with a hydrogen peroxide concentration in the mixture of step (1) selected in the region of from 2.5% to 15%, in conjunction with an appropriate weight ratio of the solutions of steps (1) and (2).

The solution of step (2) is preferably introduced into the reaction medium over a period of at least 10 minutes to 120 minutes and often from 15 to 60 minutes. Thereafter, the mixture may be permitted to continue reacting, for example for up to about 4 hours. Longer reaction times are permissable. The reaction mixture is preferably maintained at a temperature in the range of below about 30° C. to about 5° C., and particularly from about 20° to 25° C. at least for peroxyacids according to formula (1) herein, in order to enhance product purity and retain reasonable reaction rates.

Peroxyacid product can be recovered from the reaction mixture by a combination of techniques. It can be cooled, for example to below about 5° C., and additionally or alternatively the acidity of the mixture can be lowered, preferably to below about 40% and for example to about 5 to about 30%. The two operations can be combined by quenching the mixture with iced water. The resultant solid precipitate can be separated from the mother liquor by conventional apparatus such as filters and centrifuges.

The attention of readers not skilled in the art of peroxygen chemistry is directed to the potentially hazardous nature of peroxidation reactions and their products, to the need to take appropriate safety precautions at all times and to control the reaction conditions so as to ensure that the reaction mixture never at any time excedes its SADT, self accelerating decomposition temperature and to carry out any initial tests on a very small scale.

Notwithstanding the above general warning which is of particular relevance to many peroxyacids, the peroxyacids of the instant invention are characterised by their generally benign properties, specifically their relatively high stability and resistance to decomposition which they combine with superior bleach performance.

The imido-containing carboxylic acids, if they are not readily available, can themselves be obtained by a conventional condensation between a suitably substituted aromatic-1,2-anhydride and the corresponding phenyl substituted aminoalkanoic acid.

Whilst the instant invention relates primarily to the peroxyacids themselves, it will be understood that it is possible to form magnesium salt derivatives of the peroxyacids by neutralisation using magnesium oxide or similar compounds in media rendered alkaline to above the pKa of the peroxyacid and recovery of the product that is permitted or induced to precipitate out. These corresponding salts share the stability and performance of the peroxyacids themselves, and accordingly could be employed. However, it will be recognised that it is of benefit for washing and bleaching purposes to avoid the un-necessary introduction of cations that directly contribute to water-hardness, such as magnesium. This particular benefit is inherent in the use of the instant selection of peroxyacids, but is not retained when the corresponding magnesium salt is used. Such magnesium salts tend to enjoy a markedly higher solubility and rate of dissolution than the acid form from which they are derived. Thus, it will be immediatedly recognised that where it is beneficial to employ a peroxyacid having high water solubility, the user may prefer to employ the magnesium salt form of the invention peroxyacids. Where it is desirable to employ peroxyacids having relatively low water solubility, so as to minimise or eliminate bleach spotting problems, the acid form of the invention peroxyacids may be preferred. Hereinafter, unless the context clearly demands otherwise, a reference to the use of an invention peroxyacid or compositions containing it includes a reference to use of the corresponding magnesium salt.

The percarboxylic acids according to the instant invention are particulate solids and they can be employed by themselves or can be incorporated as an active bleach component in bleaching or washing compositions containing a range of other ingredients, the selection and amounts of which are at the discretion of the formulator and determine the name for the compositions.

For bleach or bleach additive compositions, the peroxyacid normally comprises from 1 to 80%, and often from 5 to 50%, all %s herein being w/w of the respective composition unless otherwise stated. It will be recognised that the invention peroxyacids are not only very effective against hydrophobic stains, but they also retain very good performance against hydrophilic stains such as tea or red wine, as can be recognised from a number of comparative trials under low temperature wash conditions in which they performed similarly to a benchmark peroxide, DPDDA. Thus, beneficially, there is no need to employ a peroxyacid other than one according to the instant invention to obtain good performance against both hydrophilic and hydrophobic stains. None the less, if desired, an additional peroxyacid may be used as a co-bleaching agent. Some benefit may be obtained by co-use of any peroxyacid which shows superior performance against hydrophilic stains. In a mixture of peroxyacids, the invention peroxyacid preferably comprises at least 10 mole % of the peroxyacids.

The remainder, 99 to 20%, of the bleach or additive composition comprises a diluent either by itself or together with a minor amount, such as up to 20% in total of optional components such as peroxygen stabilisers, surfactants, etc as indicated subsequently herein. The skilled reader will recognise that many of the diluents described herein as being suitable have hitherto been described as one or other of desensitising diluents or stabilising diluents or exotherm control agents in conjunction with named prior art organic peroxyacids such as DPDDA. Whilst the presence of such diluent compounds may have been necessary to perform that function for those prior art peroxyacids, it is a significant feature of the invention peroxyacids that the presence of the same diluents is optional and in practice their selection can be based upon any other desirable feature of those compounds, such as their cheapness or their advantageous washingor detergent-enhancing properties.

The diluent is often a salt selected from anhydrous or hydrated alkali or alkaline earth metal salts of halogen-free acids, and particularly of mineral acids, including salts of sulphuric, and ortho, pyro or hexa-meta phosphoric acids. Preferably, the metal is selected from sodium, potassium and magnesium and in many instances is sodium. Hydrated, partially hydrated or anhydrous sodium sulphate is often chosen in view of its widespread availability, its properties and its cost. It will be recognised, though, that use of a phosphate salt may be preferred in view of its known capabilities of acting as a detergent builder, which can complement especially an unbuilt washing composition.

Other inorganic compounds that are suitable for use as diluents include ortho and meta boric acid and alkali metal salts thereof, and especially sodium salts. Such compounds can buffer solutions of the bleach or additive composition to a pH in the immediate region of the pKa of the peroxyacid and consequently optimise bleach activity. The boric acids have also been used as exotherm control agents in compositions containing peroxyacids such as DPDDA that need to be protected against a tendency to decompose in an otherwise uncontrollable fashion if allowed to reach a quite low threshold temperature, but that property is unnecessary in conjunction with the invention peroxyacids on account of the safe nature of these selected imido peroxyacids.

Other suitable inorganic diluents include alkali metal carbonates/bicarbonates, aluminium salts of the above-identified mineral acids, and natural or synthetic alumino-silicates, e.g. zeolites A, X and Y, often in sodium form, or swelling clays like bentonire, or a layered silicate as in EP-A-0 337 217. It will be clear that many of said diluents also enjoy the status of builders in washing compositions, and that each accordingly can perform its known functions such as hardness removal or peptising when employed in bleach compositions. When the bleach composition is intended as a scour, at least a proportion of the diluent and preferably at least half of the diluent comprises abrasive powdered materials, including silica, quartz, marble dust or kieselguhr.

A further and rather different class of suitable inorganic diluents comprises alkai metal or alkaline earth metal halides, especially chlorides and/or bromides and particularly sodium chloride, or sodium bromide or a mixture of the two. By employing this class of diluents as at least a part of the diluents, the composition can generate in solution during use of the composition a halide such as chlorine or bromine which can complement the bleaching/sanitising effect of the invention imido peroxyacids.

The diluent can comprise a hydrogen peroxide— developing solid persalts, or an inorganic persulphate, preferably in an amount of not more than 50% w/w of the composition. The term "persalt" herein relates primarily to alkali metal perborates, percarbonates and perphosphates, and especially the sodium salts, which generate hydrogen peroxide or the HOO- anion depending on the solution pH, in situ and includes other hydrogen peroxide adducts which can do likewise. Preferred persalts include sodium perborate monohydrate or tetrahydrate and sodium percarbonate. Persalts include adducts with urea and related compounds, adducts with certain aluminosilicates and addition compounds with alkali/alkaline earth metal sulphate/chlorides in specified ratios. It will be recognised that the use of persalts as diluent, such as in at least 10% of the composition, enables the composition to be effective throughout a range of temperatures from ambient up to about 100° C.

In one more specialised type of bleaching compositions, namely effervescent compositions, which are often intended primarily for cleansing dentures, but which can also be employed for many other purposes, the diluent for the invention peroxyacids preferably contains a gas generating system and if necessary a pH regulator. Compounds that are suitable for gas generating systems and as pH regulators are well known in conjunction with existing peroxyacids, and are described in EP-A-0 133 354 in the name of Interox Chemicals Limited. The gas generating system often provides from 10 to 50% and comprises either a carbon dioxide generating combination of an alkali metal carbonate or bicarbonate with a solid water-soluble acid, and especially an organic acid selected from tartaric, citric, lactic, succinic, glutaric, maleic, fumaric and malonic acids, preferably in an equivalent mole ratio of from 1.5:1 to 1:1.5 and especially at about 1:1, or an oxygen-generating compound such as anhydrous sodium perborate. The pH regulator often comprises 5 to 40% of the composition. To provide acidic conditions, it can comprise one or more of the aforementioned organic acids in an appropriate excess amount, or sulphamic acid or alkali metal bisulphates, and to provide alkaline conditions, it can comprise alkali metal silicates or excess carbonate/bicarbonates. Selection of the percarboxylic salt form can be advantageous in such compositions.

In the main, the foregoing diluents have been inorganic. However, the invention peroxyacids can be diluted, if desired, with a range of organic substances, including hydrocarbon waxes, alkyl C1 to C6 esters of aromatic mono or di carboxylic acids, solid starches, gelatines and dextrins.

The bleach compositions can also contain, as indicated before, minor components such as peroxyacid stabilisers. The breadth of compounds suitable for this purpose is well-known in this art. These are often organic chelating compounds that sequester metal ions in solution, particularly most transition metal ions, which would promote decomposition of any peroxygen compounds therein, and many suitable ones being classified in the literature as carboxylic acid, hydroxycarboxylic or aminocarboxylic acid complexing agents or as organic amino- or hydroxypolyphosphonic acid complexing agents, either in acid or soluble salt forms. Representative stabilisers expressed in acid form include picolinic acid, dipicolinic acid, quinolinic acid, gluconic acid, hydroxyethylene di phosphonic acid, and any compound satisfying the general formula:

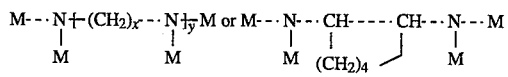

in which M represents either —CH$_2$—CO$_2$H or —CH$_2$—PO$_3$H, x represents an integer selected from 1 to 6, and preferably is 2, and y represents an integer selected from 0, 1, 2 or 3. Within this general formula especially preferred stabilisers include ethylenediamine tetra acetic acid (EDTA), ethylenediamine tetrakis (methylenephosphonic acid) (EDTMP), diethylenetriamine pentakis (methylenephosphonic acid) (DTPMP) and cyclohexylene-1,2-diamine tetrakis (methylenephosphonic acid), (CDTMPA). The amount of stabiliser is often up to 5% of the composition and in many instances is selected in the range of from 0.05 to 1%.

If present at all, a surfactant is present in bleaching or additive compositions only in a small amount, such as up to about 5% and in many instances from 0.1 to 2% of the composition. It can be selected from the surfactants described subsequently herein for washing compositions.

The invention bleaching compositions will often comprise particulate mixtures, which can be stored loosely in conventional waxed boxes, or alternatively be enclosed inrupturable pouches or in porous or perforated bags or sacs through which bleaching solution can penetrate. Such mixtures can be obtained by dry blending the particulate components, or they can be aggregated using conventional agglomeration or granulation techniques, using water or a removable solvent and optionally a granulating aid hitherto described for use with an organic peroxyacid. Alternatively, by virtue of their demonstrated ability to withstand pressure, all but the least resistant invention peroxyacids can be compressed in tablets and like bodies. Accordingly, it is possible to provide peroxyacids in easy to use predetermined dosage levels for the end user.

The bleaching compositions can be used by themselves, such as in a pre-wash bleach or a post-wash rinsing stage of a multistage laundry process or in cleansing both absorbent or non-absorbent (sometimes called "hard") surfaces. They are more usually employed in conjunction with a washing composition based upon surfactants. Naturally, surfactants and optional ingredients of washing compositions can be premixed with the instant bleaching compositions to form bleach-containing washing compositions.

The peroxyacids of the present invention may also be suspended in particulate form in aqueous acidic bleach compositions, typically in a proportion from about 0.5 to 15% w/w. Ranges of acidic bleach formulations have been described in published literature, including patent literature, incorporating particulate DPDDA and containing various materials such as thickeners or liquid structuring components which regulate the settling of the peroxyacid particles or components to regulate the pH of the composition, for example to the region of about pH 4. Suspended peroxyacid formulations of the present invention can be obtained by substituting the invention imido peroxyacids in similar amounts and particle sizes for DPDDA in such ranges of formulations.

Washing compositions according to this further aspect of the present invention contain from 0.5 to 50% of the invention imido peroxyacids, from 1 to 90% surfactant, from 0 to 90% detergent builder, from 0 to 90% diluent and from 0 to 20% minor components. It will be recognised that the composition of the invention washing compositions range within very broad limits. Choice of the peroxyacid in acid form can be beneficial herein, in order to minimise or avoid spotting problems that can occur if excessive local concentrations of active bleach should be allowed to remain in contact with a dyed fabric for too long.

In many preferred compositions according to the present invention, one or more of the composition components are selected within the following narrower bands:

| | |
|---|---|
| imido peroxyacid | 1 to 25%, particularly 2 to 10% |
| surfactant | 2 to 40%, particularly 5 to 25% |
| builder | 1 to 60%, particularly 5 to 40% |
| diluent | 1 to 70%, particularly 5 to 50% |
| minor components | 1 to 10% in total. |

The surfactants for incorporation in solid compositions of the present invention can be selected from particulate or flaky anionic, cationic, non-ionic, zwitterionic, amphoteric and ampholytic surfactants and can be either natural soaps or synthetic. A number of suitable surfactants are described in chapter 2 of "Synthetic Detergents" by A Davidsohn and B M Milwidsky (6th edition) published in 1978 by George Godwin Ltd and John Wiley & Sons, incorporated herein by reference. Without limiting to these surfactants, representative sub-classes of anionic surfactants are carboxylic acid soaps, alkyl aryl sulphonates, olefin sulphonates, linear alkane sulphonates, hydroxy-alkane sulphonates, long chain and OXO alcohol sulphates, sulphated glycerides, sulphated ethers, sulpho-succinates,alkane sulphonates, phosphate esters, sucrose esters and anionic fluorosurfactants; representative classes of cationic surfactants include quaternary ammonium or quaternary pyridinium salts containing at least one hydrophobic alkyl or aralkyl group, representative classes of nonionic surfactants include condensates of a long chain alkanol with either polyethylene oxides or with phenols, or condensates of long chain carboxylic acids or amines or amides with polyethylene oxide, and related compounds in which the long chain moiety is condensed with an aliphatic polypol such as sorbitol or condensation products of ethylene and propylene oxides or fatty acid alkanolamides and fatty acid amine oxides; representative classes of amphoteric/zwitterionic surfactants include sulphonium and phophonium surfactants, optionally substituted by an anionic solubilising group. The proportion of surfactant, expressed as a fraction of all the surfactant present is often from 2/10 to 8/10ths anionic, from 0 to 6/10ths nonionic, and from 0 to 3/10ths for the other surfactants.

It will be recognised by the skilled reader that many of the classes of diluent described herein above for use in bleaching compositions are alternatively referred to as detergent builders in view of their ability to aid the wash performance of detergents. These include specifically alkali metal phosphates, particularly tripolyphosphate but also tetrapyrophosphate and hexametaphosphate, especially the sodium salt of each, alkali metal, preferably, sodium carbonate, alkali metal, preferably, sodium borates, and the zeolites A, X and Y and clays like bentonite. Amongst organic compounds, the chelating compounds which were described herein as peroxygen stabilisers can also function as detergent builders. Particularly preferred chelating builders include nitrilotrisodium trisacetate (NTA), EDTA, EDTMP and DTPMP. Such chelating builders can be employed in a relatively small amount as an augmenting builder and peroxygen stabiliser, such as of 1 to 10%, or in cooperative partnership of equals in conjunction with a phosphatic or zeolitic or clay builder, the weight ratio of chelating to inorganic builders often being from 4:1 to 1:4, or alternatively they can be employed as the principal builder in amounts of up to 40% such as in the range of 5 to 30% of the washing composition.

The other types of compounds that have been indicated to be suitable for use as diluents in a bleaching composition, can also be employed for the same primary purpose and secondary purpose, if any, in washing compositions, although it will be recognised that the presence of an effervescent system in washing compositions is comparatively rare. For the avoidance of doubt, persalts can be incorporated in the instant washing compositions, preferably in an amount of up to 30%, such as 1 to 20%, and sometimes in a weight ratio to peroxyacids in the composition of from 5:1 to 1:5. A diluent commonly present in these washing compositions is sodium sulphate, often from 5 to 50%, because it also functions as a processing aid. The previously mentioned salts that enable a halogen to be generated in situ can likewise be present in the washing compositions, which can then enjoy the alternative name of sanitising compositions.

The washing compositions can contain a number of optional components, sometimes alternatively called auxiliary agents. These agents which can each individually be included include soil anti redeposition agents (SARDs), dye transfer inhibitors, optical brightening agents (OBAs), stabilisers, corrosion inhibitors, bactericides, dyes, perfumes, foam enhancers, foam inhibitors, pH regulators and absorbents. The amount for each auxiliary agent is often selected in the range of 0.02 to 0.2% for dyes and perfumes and from 0.1 to 2% for each of the other auxiliary agents. It is preferable to select auxiliary agents which are known not to interact with peroxygen compounds during storage or to coat the agent with or incorporate the agent in a known fashion within a matrix of a dispersible material such as a wax or the many other film-forming substances proposed in the literature for separating organic peroxygen compounds from co-components, e.g. in EP-B-00 27 693 to Interox Chemicals Limited. Such substances can also function as granulating aids (binders), if the invention compositions are granulated or agglomerated. Examples of suitable SARDs include carboxymethyl cellulose particularly the sodium salt, polyvinylpyrrolidone and examples of OBAs include derivatives of diaminostilbene sulphonic acid and 1,3-diaryl-2-pyrazolines and aminocoumarins.

The invention washing compositions can be dampened or dissolved in a little water for cleaning and disinfecting non-adsorbent surfaces such as walls, floors, work surfaces, vessels, baths, sinks and sanitaryware of metal, plastics, ceramics or glass, wood and rubber.

One of the main intended uses of the washing compositions is to cleanse and indeed also disinfect soiled adsorbent materials such as household laundry items or other articles made especially from cotton, rayon, flax or wool or manmade fibres such as polyesters or polyamides. The cleansing processes can be carried out at ambient temperature or at elevated temperature up to the boiling temperature of the washing solution. The more preferred washing temperature for laundry is from 30° to 60° C. In laundering, it is desirable to introduce sufficient washing composition and/or bleach additive composition to provide at least 5 ppm avox from the imido peroxyacid, and often from 10 to 50 ppm avox, ppm indicating parts per million by weight and avox indicating available oxygen. This can often be provided by the introduction of the invention washing composition selected in the range of 1 to 25 gpl, or bleach additive composition selected in the range of from 0.5 to 10 gpl, the selection taking into account the concentration of imido peroxyacid therein. The presence of persalts in the wash can supplement avox levels, for example by amounts of from 10 to 100 ppm avox. In use, depending upon whether and the extent to which alkaline materials, especially builders, are present in the composition itself or in any accompanying washing composition, the compositions generate upon dissolution either a mildly acidic through to especially a mildly alkaline pH. It is preferred to generate a pH of from 7.5 to 9.5 and especially around pH of 8 to about 9.0 to optimise bleaching/washing performance from the peroxyacid.

For use in disinfection, it is often preferable to employ an invention peroxyacid concentration of up to 200 ppm avox and in many instances from 25 to 100 ppm avox. It is also suitable to employ a solution spanning neutrality, from mildly acidic, such as at least pH 4 up to mildly alkaline, such as pH 9, though more acidic pHs such as from pH 1 to 4 can also be contemplated. In order to attain a pH in such a range, the choice of builders/diluents is so made as to avoid highly alkaline materials and instead select those that generate mild acidity or alkaninity such as sodium dihydrogen phosphate.

The washing processes for laundry can be carried out in currently available equipment. Washing times typically range from about 10 minutes to 30 minutes. Hand washing and extended steeping using solutions of the invention compositions can alternatively or additionally be used. Specialist variations of the invention compositions, such as those intended for happy sanitisation/cleansing or for denture cleansing are preferably used in the accepted manner for prior art compositions, for example steeping a soiled happy in a warm peroxyacid-containing solution for several hours before washing it using laundry techniques.

Having described the invention in general terms, specific embodiments will now be described more fully by way of example only.

EXAMPLE 1

Preparation of imido peroxyacids. In this Example, the reaction equation for the acid catalysed reaction was:

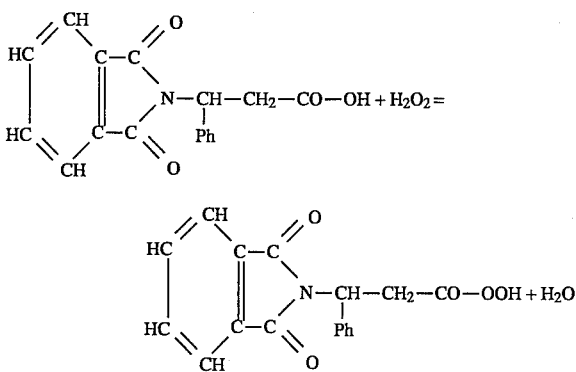

The general preparative route adopted for the first preparation of this peroxyacid was as follows:

An imido carboxylic acid starting material was prepared by condensing phthalic anhydride with 3-aminopropanoic acid. The results from IR and NMR analyses confirmed the presence of phthalimide and carboxylic acid moieties, and acid titration confirmed that there was only one acid group per molecule. The measured melting point of the carboxylic acid was 168°–70° C. confirmed that the desired starting material had been obtained.

A weighed amount of 3-phthalimido-3-phenylpropanoic acid (10 g) was introduced into stirred methanesulphonic acid (55 mls) in a beaker, forming a solution or suspension depending upon the solubility of the reactant, and the mixture was cooled to 3° C. in a water/ice bath. Hydrogen peroxide assaying 85% w/w approx. aqueous solution, was pumped via a peristaltic pump with continued stirring into the reaction mixture progressively during a period of about 5 to 10 minutes at a rate controlled so that the mixture's temperature did not rise above 5° C., until a total amount of 3.5 moles per mole of carboxylic acid had been introduced, i.e. a 2.5 molar excess compared with the stoichiometric amount. The reaction mixture was then stirred at about 20° C. for about 60 minutes. By the end of the reaction a substantial fraction of the carboxylic acid had been oxidised to the corresponding peroxycarboxylic acid, which precipitated out of solution.

The reaction mixture was poured into about 3 times as much iced water per volume of reaction mixture, filtered and the filter cake washed twice with about 30 to 40 mls of cool water each time and finally air-dried.

The yield of solid was 9.5 g having an avox content of 4.95% which indicates a purity of 96/97% (theoretical avox 5.14%) and a melting point of 116°–118° C. The peroxyacid product is 3-phthalimido-3-phenyl-peroxypropanoic acid (PPPA), having the structural formula given in the reaction equation.

The avox was measured by a standard technique in which a measured weight of sample was dissolved in acetic acid, if necessary augmented with dichloromethane to ensure that the sample is completely dissolved. The sample is then contacted with a measured amount of sodium carbonate stabilised sodium iodide, in the presence of ferric chloride, allowed to react for 10 minutes in the dark, and the resultant solution is titrated against standardised sodium thiosulphate solution until the pale yellow coloured solution becomes colourless. The result is compared with a corresponding titration against a blank solution, and from the difference the avox is calculated.

The isolated peroxyacid was analysed by conventional IR and NMR techniques to confirm the presence of imido and percarboxylic acid groups in the product molecule. Three significant infra-red peaks were found. Two peaks were observed with centres at 1770 and 1710 cm-1, which correspond to a five membered imide ring. The third peak was observed having a centre at 1760 cm-1, indicative of carbonyl stretching in a peroxycarboxylic acid which is a substituent of an alkylene chain. It was also observed for the product that there was a substantial absence of peaks at about 3360 cm-1, or in the regions of 1640 to 1675 cm-1, and 1530 to 1545 cm-1, which would have indicated the presence of an amide group obtained by opening of the imide ring during the peroxidation reaction. The spectra for the corresponding imidocarboxylic acid starting materials contained two significant peaks, a sharp peak at 1770 cm-1 and a broad peak at about 1720 cm-1, which correspond to the two peaks for the imide structure, but the second one merging with a similarly located carboxylic acid peak. Thus, from the IR data, it can be deduced that the product retained its phthalimido structure and gained a percarboxylic acid group.

The peroxyacid was analysed by proton NMR in $CD_2Cl_2$. The characteristics peaks for the compound, together with an indication whether they are singlet (s), doublet (d), triplet (t) or multipier (m), are listed in Table 1 below.

TABLE 1

| Chemical shifts | Peak attributed to H in |
|---|---|
| 12–9.5 broad | —CO—OOH |
| 7.8 m | 2 × phthalimido H |
| 7.67 m | 2 × phthalimido H |
| 7.52 d | 2 × phenyl H |
| 7.3 m | 3 × phenyl H |
| 5.8 dd | H on carbon substituted by phenyl |
| 3.9 dd | H on carbon alpha to carbonyl |
| 3.3 dd | the other H on carbon alpha to carbonyl |

It will be recognised that the NMR data given in Table 1 confirms the structures implicit from the reaction equations, the avox test and the IR scan, and in particular the existence of the asymmetric carbon.

EXAMPLE 2

In this Example, PPPA was made by an alternative process employing a sulphuric acid reaction medium.

A reaction medium having an acidity of 75% was made in step (1) by mixing with agitation and cooling to below ambient temperature in an ice bath sulphuric acid (98% w/w, 59.2 g), aqueous hydrogen peroxide (85% w/w, 3.6 g, 0.09 mole) and water (demineralised, 17.6 g). In step (2), a further sample of the carboxylic acid PPA (5 g, 0.169 mole)

was dissolved in concentrated sulphuric acid (98% w/w, 15 g). Thereafter, in step (3), the solution of PPA was introduced at a constant rate into the reaction medium over a period of 20 minutes using a diaphragm pump and demineralised water (4.6 g) was introduced separately and simultaneously at a constant rate into the reaction medium, using a peristaltic pump, thereby maintaining the acidity of the mixture at 75%. The mixture was agitated, and maintained by cooling at a temperature of 25° C. The reaction was permitted to continue under the same conditions for a further hour, whereupon a solid precipitated out of solution. The solid was filtered and water washed until the filtrate was about pH 3. The resultant creamy white solid had an Avox of 4.26% and a purity of approximately 83%.

Tests to characterise the properties of the invention peroxyacid product were carried out as follows:

Storage Stability

In this test, weighed samples of the peroxyacid are individually sealed in glass phials with a bubbler cap that permits excess internal pressure to vent to atmosphere, and stored in a dark chamber that is thermostatically controlled to 32° C. The avox of the peroxyacid is measured shortly after its preparation i.e. $A_0$ and after predetermined storage intervals, $A_s$, the measurement being made on entire individual samples. The stability results of stored samples are $A_s/A_0$, quoted as a percentage, the higher the better.

Avox is measured using the same method as described hereinabove.

It will be recognised that the storage stability of the peroxyacid by itself is an extremely important characteristic of a peroxyacid, not only because the compound is likely to be stored in that way before it is encorporated in specific compositions, but also because represents the intrinsic stability of the compound, the maximum attainable even if the remaining components of compositions containing it are benign.

A+ indicates that the compound is according to the invention whereas a − indicates that it is present by way of comparison.

TABLE 2

| Compound | Proportion of avox remaining after | | |
|---|---|---|---|
| | 1 week | 4 weeks | longest/n weeks |
| + PPPA | 94 | 94 | 85/12 w |
| − DPDDA | 97 | 85 | |

From Table 2, it can be seen that PPPA had very good inherent storage stability.

Hazard Rating

Two tests are described below to demonstrate the hazard rating of the peroxyacid. They are respectively an impact sensitivity test and a pressure-time test.

In the impact sensitivity test, a weight (in kg) is dropped once from a measured height (in cm) onto a fresh sample of the peroxyacid held in the anvil. The sample is thus subjected to an impact, normally expressed as kg-cm (1 kg-cm= $9.8 \times 10^{-2}$ J) that is proportionate to the height and weight. The test is carried out many times at each impact strength, and is observed to see whether the sample responds, by charring, emitting smoke or at worst undergoing a minor explosion. The tests start at a low impact strength and are continued at increasing strengths until the limiting result is obtained, being the earlier of either 50% of the tests at that impact strength give positive results or a figure of 500 kg-cm is reached, which past experience indicates to represent a non-impact-sensitive product. The limiting result in kg-cm is shown in Tables summarising the results, the higher the better.

In the pressure-time test, 2 g samples of the test material is placed inside an 18 ml steel bomb, and its decomposition initiated. The consequential rise in pressure is monitored and plotted or displayed against elapsed time, expressed in milliseconds. In Table 3, the time is given for the pressure in the bomb generated by the sample to increase from 100 to 300 psi, i.e. from $6.895 \times 10^5$ Pa to $2.068 \times 10^6$ Pa, the longer the better. The symbol oo indicates that a pressure of 300 psi was not reached, i.e. a period of infinite duration. By way of interpretation, a time of less than 30 milliseconds indicates that the material is potentially explosive, a time of 30 to 60 milliseconds indicates that it is marginally explosive, and to allow a safety margin, it is preferred to be around 100 milliseconds or longer.

TABLE 3

| | Hazards rating results | |
|---|---|---|
| Compound | Impact kg-cm | p-t msec |
| + PPPA | >500 | oo |
| − DPDDA | >500 | 30 |

From Table 3, it can be seen that the invention imidoperoxyacid PPPA was non-hazardous as demonstrated by both a result of over 500 kg-cms in the impact test and a non-attainment of a pressure of 300 psi in the pressure-time test, and indeed also that it is significantly safer than the reference compound DPDDA.

Bleach/washing Evaluation

The effectiveness of the invention and comparison peroxyacids was tested by washing swatches of cotton cloth that had been preimpregnated in a standard manner with one of four representative stains, tea, red wine, grass and blue polish. The evaluations were carried out in a laboratory scale washing machine, a "Tergotometer" (Trade Mark) available from the US Testing Corporation, under identical standardised conditions. The washing solution comprised local Cheshire tap water, hardness of about 160 to 180 ppm hardness as calcium carbonate, in which was dissolved a peroxyacid-free washing composition at 6.5 g/l. Composition NSPA used in all trials had the approximate analysis:

| Composition Component | DBPF % w/w |
|---|---|
| Anionic surfactant | 9 |
| Nonionic surfactant | 8 |
| Sodium carbonate | 3 |
| Sodium sulphate | 19 |
| odium phosphate | 46 |
| Sodium silicate | 10 |
| Sodium Borate | 4 |
| Water | balance |

A weighed amount of peroxyacid was introduced into the washing solution to provide a peracid avox of 25 ppm therein, assuming total dissolution. This corresponds to a molar concentration of $1.56 \times 10^{-3}$M monoperoxyacid. The washing solution was kept at pH 9 and at 40° C. during the washing period of 20 minutes. The swatches were then rinsed and dried and the extent of stain removal was determined by comparing the reflectance of the washed cloth, $R_w$, with that of the pre-washed, stained cloth, $R_s$, and that of the unstained cloth, $R_u$. The measurements were obtained using an Instrumental Colour System "Micromatch" (Trade Mark) reflectance spectrophotomer equipped with a Xenon lamp filtered through a D65 conversion filter to approximate to CIE artificial daylight. Stain Removal, expressed a s percentage, was calculated using the formula:

$$\%SR = 100 \times [R_w - R_s] / [R_u - R_s]$$

It will be recognised that by demonstrating the washing capability of the peroxyacids in this way, the tests using the invention peroxyacids are in themselves examples of washing processes according to other aspects of the present invention. Similarly, since the swatches had not been stored in sterile conditions before being washed, the washing procedure will act simultaneously to disinfect them.

The results quoted below are the mean of two evaluations. Comparative results on the same stained cloths using the washing composition by itself, i.e. without any added peracid, are designated "base".

TABLE 4

| Ex/Comp No | Peracid employed | % Stain Removal | | | | |
|---|---|---|---|---|---|---|
| | | Red Wine | Grass | Tea | Blue Polish | Average Removal |
| C3 | base only | 71 | 71 | 54 | 53 | 62 |
| C4 | PIPCA | 94 | 86 | 80 | 56 | 79 |
| C5 | DPDDA | 89 | 86 | 78 | 62 | 79 |
| 6 | PPPA | 92 | 95 | 77 | 75 | 85 |

From Table 4, it can be seen that the invention peracid is a very effective bleaching agent at hand-hot washing temperatures, not only by comparison with a peracid-free base composition, but also when measured against both PIPCA and DPDDA. The main advantage is detectable against grass and polish stains.

Bleach Additive Formulations

Representative formulations are made by dry mixing particulate invention peroxyacid with a premixture of the remaining components. The peracids have the names given in Tables 1 and 2. LAS represents a linear alkyl benzene sulphonate, sodium salt, average alkyl length of C11.5, and OBA represents an optical brightening agent.

TABLE 5

| Example No Particulate Components | 8 % w/w | 9 % w/w | 10 % w/w |
|---|---|---|---|
| PPPA (4.95% avox) | 8.1 | 32.3 | 64.6 |
| LAS | 3 | 4 | 5 |
| OEA + chelate | 0.2 | 0.2 | 0.2 |
| Sodium sulphate | 88.7 | 63.5 | 30.2 |

Dosing of these formulations each at 1.25 gpl provides respectively avox concentrations in solution of aproximately 5 ppm, 20 ppm and 40 ppm. Solid bleach additive compositions containing a pH buffer to lower the solution pH closer to about pH 8.5, and hence improve stain removal are made by replacing about 10% w/w of the sodium sulphate by boric acid.

Washing Formulations

Representative washing compositions according to the present invention are made by dry mixing the particulate invention peroxyacid with a blend of the other components shown in Table 6. The abbreviations STPP and PBS1 represent respectively sodium tripolyphosphate and sodium perborate monohydrate. The chelating agent is EDTMP, ethylene diamino (tetramethylene phosphonate), Na salt.

TABLE 6

| Example No Components | 11 % w/w | 12 % w/w | 13 % w/w | 14 % w/w | 15 % w/w | 16 % w/w |
|---|---|---|---|---|---|---|
| PPPA (4.95% avox | 2.5 | 5.0 | 7.6 | 3.8 | 6.3 | 8.8 |
| LAS | 7.0 | 9.6 | 8.6 | 7.0 | 6.0 | 6.0 |
| Alcohol Ethoxylate | 5.1 | 3.8 | 5.7 | 2.5 | 6.0 | 7.0 |
| STPP | 34.0 | 26.1 | | 40.0 | 30.0 | 30.0 |
| Zeolite A | | | 22.5 | | | |
| Carboxylate builder | | 2.0 | 15.0 | | | |
| Sodium sulphate | 13.5 | 36.3 | 21.8 | 17.4 | 22.1 | 14.1 |
| Sodium silicate | 14.0 | 6.7 | 7.6 | 6.5 | 5.0 | 5.0 |
| Soap | 6.5 | | | 3.0 | 3.0 | 2.0 |
| Buffer boric acid | 10.0 | | | 10.0 | 10.0 | 10.0 |
| PBS1 | | | | | | 9.0 |
| CMC | 1.0 | 1.0 | 1.0 | 1.0 | 1.0 | 1.0 |
| Minors (Chelate + OBA + Perfume etc) | 0.4 | 0.4 | 0.4 | 0.6 | 0.3 | 0.5 |
| Water | balance | | | | | |

Use of these formulations at a concentration of 8 gpl in the washing liquor, a typical level for front loading washing machines in Europe, results in peracid avox concentrations of approximately 10, 20, 30, 15, 25, and 35 ppm respectively.

Sanitizer Formulations

Representative formulations are made by dry mixing the specified invention peroxyacids with the other components specified in Table 7.

TABLE 7

| Example No<br>Particulate Components | 17<br>% w/w | 18<br>% w/w | 19<br>% w/w |
| --- | --- | --- | --- |
| PPPA (4.95% avox) | 6.0 | 10.1 | 14.2 |
| LAS | 9.0 | 7.0 | 5.0 |
| Sodium carbonate | 20.0 | 23.0 | |
| STPP | 10.0 | 10.0 | 10.0 |
| Sodium bicarbonate | | | 26.0 |
| Sodium chloride | 46.5 | 49.2 | 44.0 |
| Borax | 8.5 | | |
| Organic chelate | | 1.2 | 0.8 |

When these formulations are dosed into a nappy (or similar article) sanitising solution in an amount of 5 gpl, the invention peroxyacids provide an avox of respectively 15, 25 and 35 ppm approximately.

Dilute Disinfectant Compositions

Particulate disinfectant compositions are made by dry mixing the components specified in Table 8.

TABLE 8

| Example No<br>Particulate Components | 20<br>% w/w | 21<br>% w/w | 22<br>% w/w |
| --- | --- | --- | --- |
| PPPA (4.95% avox) | 6.0 | 10.1 | 14.2 |
| Sodium dihydrogen phosphate | 10.0 | 10.0 | 10.0 |
| Boric acid | 5.0 | 5.0 | 5.0 |
| Corrosion Inhibitor | 1.0 | 1.0 | 1.0 |
| Perfume | 0.5 | 0.5 | 0.5 |
| Sodium sulphate | 77.5 | 74.0 | 69.3 |

When these formulations are employed at a dose level of 1 glp in an aqueous medium requiring disinfection, the concentration of avox therein is respectively 3, 5 and 7 ppm.

Disintegrating Tablet Compositions—Suitable for Dentures

Representative compositions of this type are made by dry mixing the components given in Table 9 below, and then subjecting them to compression in the mould of a tabletting machine to make tablet weighing about 4 g. The polyethyleneglycol binder av mol weight 6000 is designated PEG 6000, the disintegrant was a cross linked polyvinylpyrrolidone available under the Trademark POLYPLASDONE XL and the lubricant was sodium lauryl sulphate.

TABLE 9

| Example No<br>Particulate Components | 23<br>% w/w | 24<br>% w/w | 25<br>% w/w |
| --- | --- | --- | --- |
| PPPA (4.95% avox) | 8.6 | 10.8 | 12.8 |
| Succinic acid | 25.2 | 15.0 | 15.0 |
| Sodium Bicarbonate | | 25.5 | 40.0 |
| Sodium Carbonate | 10.0 | | |
| PEG 6000 (binder) | 6.0 | 6.0 | 6.0 |
| PVP disintegrant | 1.0 | 1.0 | 1.0 |
| Lubricant | 0.2 | 0.2 | 0.2 |
| Sodium sulphate | 49.0 | 41.5 | 25.0 |

When one tablet of composition 23, 24 or 25 is introduced into water it generates respectively 17, 21.5 or 25.5 mg avox.

We claim:

1. An organic peroxyacid which satisfies formula (1):

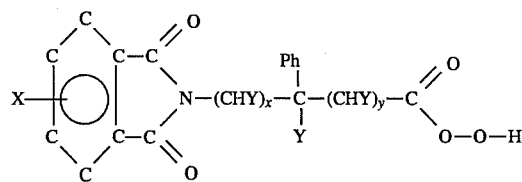

in which X represents hydrogen or a compatible non-released substituent, Y represents a group of formula $(CH_2)_zH$, x, y and z are either 0, 1 or 2, and x+y+z =1 or 2, and Ph represents a phenyl substituent, optionally substituted by a compatible non-released substituent.

2. A peroxyacid according to claim 1 in which X=H, x=0, y=1 and z=0.

3. An organic peroxyacid according to claim 1 wherein each of said compatible non-released substituents is selected from the group consisting of alkyl and halo.

4. A method for making a peroxyacid in which a carboxylic acid is reacted with aqueous hydrogen peroxide in a sulphuric acid reaction medium, said process comprising:

step (1)-mixing aqueous hydrogen peroxide with concentrated sulphuric acid to form an aqueous reaction medium having a predetermined acidity in the range of from 60% to 90% such that it is below the acidity at which the reaction medium would be hazardous if it contained the peroxyacid;

step (2)-dissolving a carboxylic acid in concentrated sulphuric acid to form an acidic solution of the carboxylic acid having an acidity higher than the acidity of the reaction medium formed in step 1; and step (3)-introducing the acidic solution formed in step (2) gradually with stirring at a temperature of below about 40° C. into the reaction medium formed in step (1), and introducing an aqueous diluent into the reaction medium to maintain the acidity of the reaction medium substantially constant whereby the peroxyacid is formed in a reaction medium having an acidity below the acidity at which the reaction medium containing the peroxyacid is hazardous.

5. A method according to claim 4 wherein the carboxylic acid has the formula:

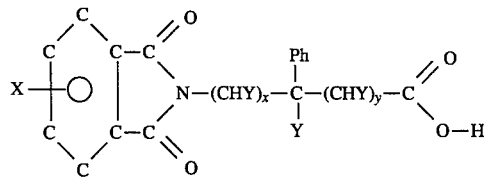

in which X represents hydrogen or a compatible non-released substituent, Y represents a group of formula $(CH_2)_zH$, x, y and z are either 0, 1 or 2, and x+y+z=1 or 2, and Ph represents a phenyl substituent, optionally substituted by a compatible non-released substituent.

6. A method according to claim 5 wherein the acidity of the reaction mixture is maintained at 70 to 75% by weight.

7. A method according to claim 5 or 6 wherein the temperature is maintained at about 20° to 25° C. during step (3).

8. A method according to claim 5 wherein each of said compatible non-released substituents is selected from the group consisting of alkyl and halo.

9. A bleach composition containing from 1 to 80% w/w of an organic peroxyacid which satisfies the formula (1):

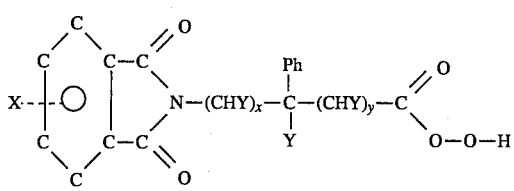

in which X represents hydrogen or a compatible non-released substituent, Y represents a group of formula $(CH_2)_zH$, x, y and z are either 0, 1 or 2, and $x+y+z = 1$ or 2, and Ph represents a phenyl substituent, optionally substituted by a compatible non-released substituent; and from 99 to 20% w/w of a diluent.

10. A bleach composition according to claim 9 wherein each of said compatible non-released substituents is selected from the group consisting of alkyl and halo.

11. A washing composition containing from 0.5 to 50% w/w of an organic peroxyacid which satisfies the formula:

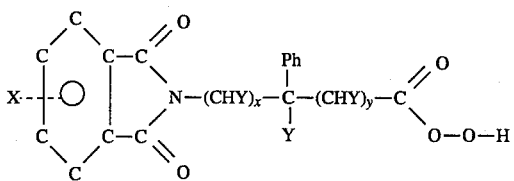

in which X represents hydrogen or a compatible non-released substituent, Y represents a group of formula $(CH_2)_zH$, x, y and z are either 0, 1 or 2, and $x+y+z = 1$ or 2, and Ph represents a phenyl substituent, optionally substituted by a compatible non-released substituent, from 1 to 90% surfactant, from 0 to 90% detergent builder, from 0 to 90% diluent and from 0 to 20% auxiliary agents.

12. A washing composition according to claim 11 wherein each of said compatible non-released substituents is selected from the group consisting of alkyl and halo.

13. In a method of bleaching in which an item to be bleached or disinfected is contacted with a bleaching composition comprising a peroxyacid bleaching or disinfecting agent, the improvement wherein said peroxyacid bleaching or disinfecting agent comprises a peroxyacid according to claim 1 or claim 2.

14. A method according to claim 13 wherein said bleaching composition comprises from 1 to 80% w/w of said bleaching agent and from 99 to 20% w/w of the diluent.

15. In a method of washing in which an item to be washed is contacted with a washing composition comprising a peroxyacid bleaching or disinfecting agent, the improvement wherein said peroxyacid bleaching or disinfecting agent comprises a peroxyacid according to claim 1 or claim 2.

16. A method according to claim 15 wherein said washing composition comprises 0.5 to 50% w/w of said bleaching agent, from 1 to 90% w/w of a surfactant, from 0 to 90% w/w of a builder, from 0 to 90% w/w diluent, and from 0 to 20% w/w of auxiliary agents.

* * * * *